United States Patent
Raji

(10) Patent No.: US 11,986,889 B1
(45) Date of Patent: May 21, 2024

(54) HELICAL TUNNELING AND FIXATION DEVICE

(71) Applicant: Oluwatodimu Richard Raji, San Francisco, CA (US)

(72) Inventor: Oluwatodimu Richard Raji, San Francisco, CA (US)

(73) Assignee: Medical Device Development, San Francisco, CA (US)

( * ) Notice: Subject to any disclaimer, the term of this patent is extended or adjusted under 35 U.S.C. 154(b) by 0 days.

(21) Appl. No.: 18/052,141

(22) Filed: Nov. 2, 2022

(51) Int. Cl.
*B23B 51/00* (2006.01)
*B23B 51/04* (2006.01)

(52) U.S. Cl.
CPC ...... *B23B 51/0072* (2013.01); *B23B 51/0426* (2013.01); *B23B 51/0467* (2022.01); *B23B 2251/248* (2013.01)

(58) Field of Classification Search
CPC .......... B23B 51/0072; B23B 2251/248; B23B 51/0426; B23B 51/0467; B23B 51/0411; B23B 51/0413; B23B 51/044; B23B 51/0468; B23G 5/182; B23G 5/20; B23G 5/184; B23G 5/188; E21B 7/003; E21B 7/005; E21B 7/201; E21B 10/44; E21B 17/22
See application file for complete search history.

(56) References Cited

U.S. PATENT DOCUMENTS

| | | | | |
|---|---|---|---|---|
| 483,210 A | * | 9/1892 | Corrigan | E21B 10/44 175/403 |
| 632,764 A | * | 9/1899 | Stephens | E21B 25/00 175/403 |
| 675,720 A | * | 6/1901 | Deemer | E21B 17/22 175/323 |
| 930,792 A | * | 8/1909 | Perry | E04H 17/124 52/157 |
| 1,022,135 A | * | 4/1912 | Heinkel et al. | B23B 51/02 408/230 |

(Continued)

OTHER PUBLICATIONS

Auger Drill Bit for Planting 1.6×16.5inch Extended Length Garden Auger Spiral Drill Bit for Planting Bulbs Flowers Planting Auger for Drill Post Hole Digger for 3/8" Hex Drill, retrieved from the internet, retrieved on Nov. 1, 2022; <URL: https://www.pricepulse.app/auger-drill-bit-for-planting-16x165inch-extended-I_us_2691331>.

(Continued)

*Primary Examiner* — Nicole N Ramos

(57) ABSTRACT

The helical tunneling device is a tool for tunneling along helical or spiral paths. Further, the tool may be used as a fixation device along helical/spiral paths, for connecting different surfaces or joints. Furthermore, the device includes associated instrumentation needed for creating such a helical path. In one embodiment, the device uses a woven flexible shaft in a helical tube to transmit rotational motion to a cutting tool. The helical tube may then be rotated independently to advance the cutting tool along a helical trajectory. In another embodiment, the device may advance helically into the created tunnel to engage, couple, and fix the relative positions of both bodies through which a continuous helical tunnel is created. Thus, the helical tunneling device is a simple and efficient tool that may be beneficial for wood working, orthopedics, metal manufacturing etc.

16 Claims, 8 Drawing Sheets

(56) References Cited

U.S. PATENT DOCUMENTS

| | | | | |
|---|---|---|---|---|
| 1,209,058 | A * | 12/1916 | Smith | E21B 10/44 175/386 |
| 1,918,353 | A * | 7/1933 | Utley | E03F 9/002 15/104.33 |
| 2,659,255 | A * | 11/1953 | Bates | B25B 21/00 408/196 |
| 2,949,618 | A * | 8/1960 | Peyser | B23B 51/108 408/112 |
| 2,969,122 | A * | 1/1961 | Steffes | B23B 51/04 175/426 |
| 3,289,290 | A * | 12/1966 | Sandor | F16B 25/0084 411/407 |
| 3,711,917 | A * | 1/1973 | Baumgras | B21F 35/00 29/896.9 |
| 3,833,073 | A * | 9/1974 | Carver | B23B 51/0453 175/173 |
| 3,848,687 | A * | 11/1974 | Funakubo | E21B 10/44 175/426 |
| 3,849,019 | A * | 11/1974 | Green | B23B 51/0426 408/209 |
| 4,135,588 | A * | 1/1979 | Wagner | E21B 10/44 175/62 |
| 4,248,313 | A * | 2/1981 | Bonca | E21B 25/04 175/239 |
| 4,639,217 | A * | 1/1987 | Adams | F27B 7/161 432/107 |
| 4,738,062 | A * | 4/1988 | Dickey | A61C 8/0022 52/157 |
| 5,265,676 | A * | 11/1993 | Harrell | E21B 31/125 166/99 |
| 5,765,437 | A * | 6/1998 | Farber | A01B 1/065 408/1 R |
| 5,765,654 | A * | 6/1998 | Burger | B23Q 11/0883 408/72 R |
| 10,010,948 | B1 * | 7/2018 | Hayden | B23P 15/32 |
| 2005/0191150 | A1 | 9/2005 | Bickford | |
| 2007/0137350 | A1 * | 6/2007 | Tateishi | B23G 1/16 74/424.87 |
| 2008/0166195 | A1 | 7/2008 | Gentry et al. | |
| 2011/0106179 | A1 * | 5/2011 | Prevost | A61B 17/7037 606/301 |
| 2013/0139657 | A1 * | 6/2013 | Jenkins | B25B 15/007 411/404 |
| 2016/0052108 | A1 * | 2/2016 | Miess | B22F 7/06 51/307 |

OTHER PUBLICATIONS

A Set 6 Pcs M3*22mm Guitar Single Coil Pickups Mount Adjust Height Flat Tail Screws & Straight Body Springs—Silver & Black, retrieved from the internet, retrieved on Nov. 1, 2022; <URL: https://www.aliexpress.us/item/2251801706113924.html?gatewayAdapt=glo2usa4itemAdapt&_randl_shipto=US>.

\* cited by examiner

HELICAL TUNNELING AND FIXATION DEVICE

FIELD OF THE INVENTION

The present invention generally relates to a device for tunneling along helical or spiral paths. Further, the present invention is a device that may be rotated independently to advance a cutting tool along a helical trajectory. Furthermore, the present invention is a device which may advance helically into a created tunnel to engage, couple, and fix relative positions of two bodies through which a continuous helical tunnel is created.

BACKGROUND OF THE INVENTION

A helix is a shape like a corkscrew or spiral staircase. It is a type of smooth space curve with tangent lines at a constant angle to a fixed axis. A helical tunnel which may be further mounted with a helical fixation device, may be utilized for connecting different surfaces, creating special fastening bonds, creating unique designs and structures etc. Accordingly, a helical tunneling device may be used for wood working, orthopedics, metal manufacturing etc. However, such a tool or device that can drill along a helical path is a rare find in the current market.

An objective of the present invention is to provide users with a device and method for tunneling along helical/spiral paths, fixation along helical/spiral paths, as well as associated instrumentation needed for creating such a helical path. In one embodiment, the present invention is a tool that uses a woven flexible shaft in a helical tube to transmit rotational motion to a cutting tool, the helical tube can then be rotated independently to advance the cutting tool along a helical trajectory. In another embodiment, the present invention is a device which may advance helically into a created tunnel to engage, couple, and fix the relative positions of both bodies through which a continuous helical tunnel is created. Additionally, the present invention may be used for creating special structures and designs. Thus, the helical tunneling device is a simple and efficient tool that may be beneficial for different industries such as wood working, orthopedics, metal manufacturing etc.

SUMMARY

The present invention is device or tool for tunneling along helical or spiral paths. Further, the present invention may be used as a fixation device along helical/spiral paths, for connecting different surfaces or joints. Furthermore, the present invention discusses associated instrumentation needed for creating such a helical path. In one embodiment, the present invention uses a woven flexible shaft in a helical tube to transmit rotational motion to a cutting tool. The helical tube may then be rotated independently to advance the cutting tool along a helical trajectory. In another embodiment, the present invention is a device which may advance helically into a created tunnel to engage, couple, and fix the relative positions of both bodies through which a continuous helical tunnel is created. Additionally, the present invention may be used for creating special structures and designs. Thus, the helical tunneling device is a simple and efficient tool that may be beneficial for various industries such as wood working, orthopedics, metal manufacturing etc.

DETAILED DESCRIPTION OF THE INVENTION

All illustrations of the drawings are for the purpose of describing selected versions of the present invention and are not intended to limit the scope of the present invention. In reference to FIG. 1 through FIG. 8, the present invention is a helical tunneling device. An objective of the present invention is to provide users a device and tool for tunneling along helical or spiral paths. Further, the present invention may be used as a fixation device along helical/spiral paths, for connecting different surfaces or joints. Furthermore, the present invention discusses associated instrumentation needed for creating such a helical path. In one embodiment, the present invention uses a woven flexible shaft in a helical tube to transmit rotational motion to a cutting tool. The helical tube may then be rotated independently to advance the cutting tool along a helical trajectory. In another embodiment, the present invention is a device which may advance helically into a created tunnel to engage, couple, and fix the relative positions of both bodies through which a continuous helical tunnel is created. Additionally, the present invention may be used for creating special structures and designs. Thus, the helical tunneling device is a simple and efficient tool that may be beneficial for various industries such as wood working, orthopedics, metal manufacturing etc.

The following description is in reference to FIG. 1 through FIG. 8. According to a preferred embodiment, the present invention comprises at least one helical rod 1 and a driving unit 2. Preferably, the at least one helical rod 1 is made of any sturdy material, such as a metal, that can traverse into a softer material to create a spiral tunnel. However, the at least one helical rod 1 may comprise any other material, size, diameter, pitch, height, components, arrangement of components, orientation etc. that are known to one of ordinary skill in the art, as long as the intents of the present invention are not altered. In the preferred embodiment, the at least one helical rod 1 comprises a flat top. More specifically, the at least one helical rod 1 comprises a first end 1*a* and a second end 1*b*, wherein the first end 1*a* is positioned opposite to the second end 1*b* across the helical rod 1. Preferably, the first end 1*a* constitutes an upper end or top end of the helical rod 1, and the second end 1b constitutes a lower end of the helical rod 1.

Figure 2:
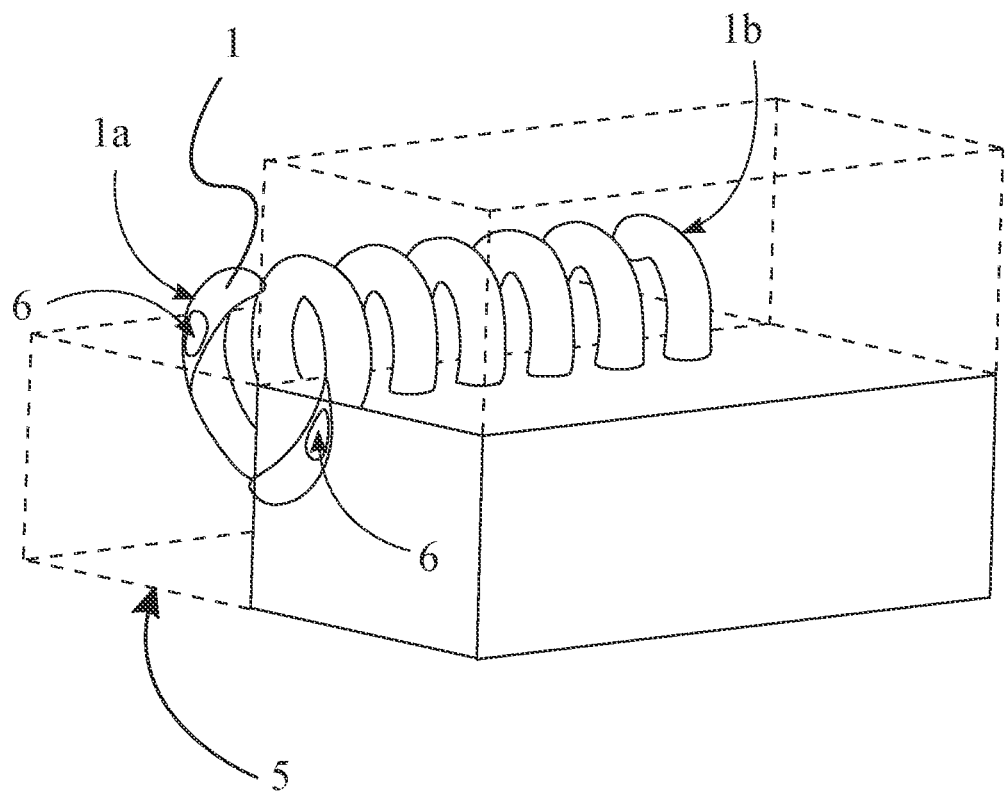
FIG. 2 is a perspective view of the present invention, wherein the helical tunneling rod is being mounted within a tunneling surface.

According to the preferred embodiment the driving unit 2 provides the driving force and rotational motion needed for the at least one helical rod 1 to advance through any surface, so as to create a helical tunnel. To that end, the driving unit 2 comprises a base plate 3 and a rigid shaft 4. Preferably, a first surface 3a of the base plate 3 is mounted onto the first end 1a of the helical rod 1, and the rigid shaft 4 is mounted onto a second surface 3b of the base plate 3, wherein the second surface 3b is positioned opposite to the first surface 3a across the base plate 3. Further, the driving unit 2 is operably coupled to the at least one helical rod 1, wherein rotating the rigid shaft 4 enables normal advancement and normal retraction of the at least one helical rod 1 along a tunneling surface 5 to create a helical tunnel. In other words, the present invention may be used to create a helical tunnel along the tunneling surface 5 with the help of the driving unit 2, connected to one end of the helical rod 1. To accomplish this, the base plate 3 of the driving unit 2 is mounted onto the helical rod 1 and rotating the base plate 3 rotates the helical rod 1 and advances the helical rod 1 along the tunneling surface 5. As seen in FIG. 2, the helical rod 1 may be mounted between multiple surfaces as a connecting fastener as well.

Figure 1:
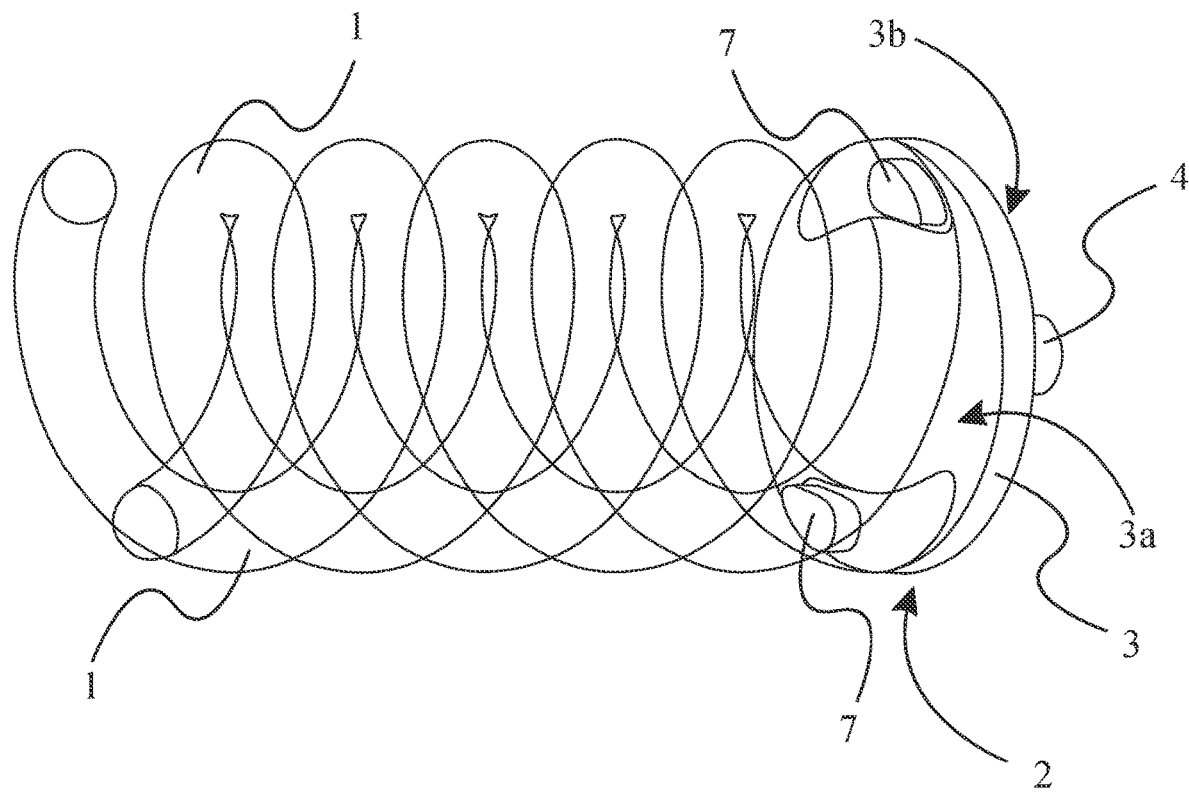
FIG. 1 is a perspective view of a first embodiment of the present invention, wherein a driving unit is connected to a solid helical rod, and the solid helical rod is shown as transparent.

As seen in FIG. 1 and FIG. 2, the at least one helical rod 1 comprises a plurality of apertures 6, and the base plate 3 comprises a plurality of protrusions 7. Preferably, the plurality of apertures 6 traverses into at least one helical rod 1 adjacent the first end 1a of the helical rod 1, and the plurality of protrusions 7 is mounted on the first surface 3a of the base plate 3. The plurality of apertures 6 are cutouts made for easier insertion and extraction of the helical rod 1 to and from the tunneling surface 5. However, the helical rod 1 may be designed with or without a cutout for insertion and extraction. Without a cutout, the device may be installed by rotating/twisting the device around its principal axis, to follow the helical tunnel created concurrently or prior. To extract, a cut out/hole may be created at the flat top surface and pushed against in the direction of curvature of the helix. The profile of the plurality of apertures 6 or cut outs may be circular, elliptical, rectangular, polygonal, triangular or a combination of the shapes. In other words, the plurality of apertures 6 may serve as a driving feature. Further, the second end 1b of the helical rod 1 or distal end of the device may be either sharp, blunt, flat, chamfered, or filleted.

Furthermore, as seen in FIG. 1, the plurality of protrusions 7 interfaces with the plurality of apertures 6 or cutout(s)/hole(s) on the at least one helical rod 1 and transmits rotational motion to the device by means of this interface. In other words, the plurality of protrusions 7 is detachably engaged with the plurality of apertures 6. Each of the plurality of protrusions 7 may be circular, elliptical, rectangular, polygonal, triangular or a combination of the shapes, and may or may not match the cut out/aperture profile. In reference to FIG. 2, the figure displays the conceptual placement or embedding of the helical rod 1 into a continuous tunnel through multiple blocks. In this embodiment, the helical rod 1 is shown to couple three blocks along a continuous helical path to each other. Additionally, two or more helical devices having the similar or different features, such as direction of twist, profile, diameter, pitch, and height, may be combined, to generate desired coupling or fixation result.

Figure 8:
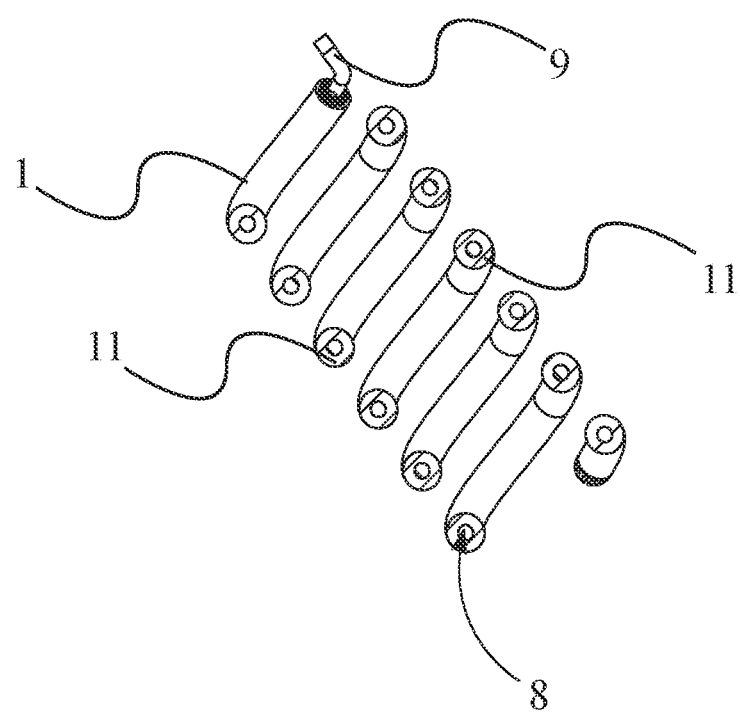
FIG. 8 is a sectional view, taken along A-A' of FIG. 7.

In reference to FIG. 3 through FIG. 8, the present invention is a device for creating helical tunnels into which a fixation device may be inserted. The device may consist of one or more entities, for creating single or multiple concentric tunnels at a time. In this embodiment, the present invention additionally comprises a cavity 8, a flexible shaft 9, and a cutting tool 10. As seen in FIG. 8, the cavity 8 is positioned within the at least one helical rod 1, and the cavity 8 traverses centrally from the first end 1a through the second end 1b of the at least one helical rod 1. In other words, the cavity 8 runs throughout the helical rod 1, making the helical rod 1 hollow. This is so that, the flexible shaft 9 may be threaded through the helical rod 1 along the cavity 8. Thus, the flexible shaft 9 follows the path of the helical rod 1 or the flexible shaft 9 conforms to the curvature of the helical rod 1. Preferably, the flexible shaft 9 consists of multiple sets of five wires, coiled or twisted along the length of a center wire, wherein each set of five wires are coiled/twisted around the previous set of wires in the opposite direction (clockwise counterclockwise), to make a form of wire rope or flexible shaft 9. However, the flexible shaft 9 may comprise any other material, size, formation method, components, arraignment of components etc. that are known to one of ordinary skill in the art, as long as the intents of the present invention are not altered. In order for the tunneling device to function smoothly, a first terminal end 9a of the flexible shaft is mounted onto the driving unit 2. The flexible shaft 9 may be driving independently, or simultaneously using a single motor coupled with a gear assembly for splitting rotation motion from the rigid shaft 4 (triangular center shaft) to two or more gears, into which the superior rigid portion of the flexible shaft(s) 9 is/are inserted. Further, the cutting tool 10 is mounted onto a second terminal end 9b of the flexible shaft 9 wherein the first terminal end 9a is positioned opposite to the second terminal end 9b across the flexible shaft 9. As seen in FIG. 3 through FIG. 6, the cutting tool 10 is positioned outside the helical rod 1, adjacent to the second end 1b of the helical rod 1. Preferably, the cutting cool 10 functions to remove material along the intended path of the tunnel. The cutting tool 10 may be designed as a bore, drill, mill or ream. Furthermore, the cutting tool 10 is attached and stabilized by means of a bearing, into which the inferior rigid portion of the flexible shaft 9 is affixed to the hollow rigid shaft of the cutting tool 10. Thus, the flexible shaft 9 conforms to the curvature of the hollow tube 1, while transmitting rotational motion and torque along its length to the cutting tool 10. However, the cutting tool 10 may comprise any other size, shape, cutting technique, number of blades etc., as long as the intents of the present invention are not altered.

As seen in FIG. 8, the present invention comprises a plurality of bearings 11. Preferably, the plurality of bearings 11 is mounted within the cavity 8, and the flexible shaft 9 is threaded through the plurality of bearings 11. This is so that the plurality of bearing 11 may help with stabilizing the rotation of the flexible shaft 9. To that end, the plurality of bearings 11 is distributed along the helical rod 1.

Figure 6:
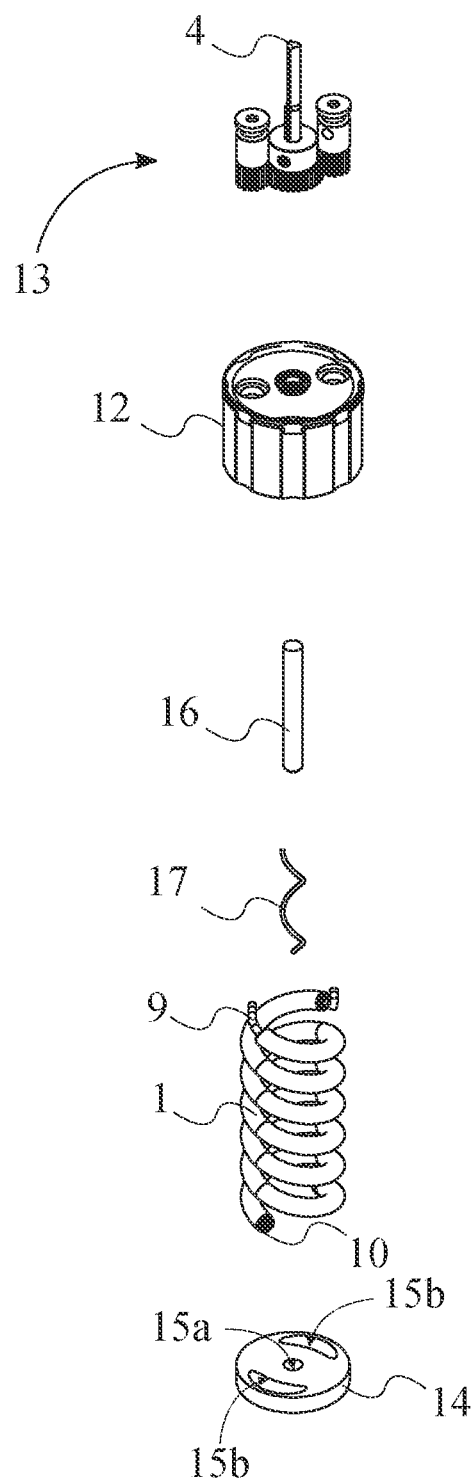
FIG. 6 is a top-front-exploded perspective view of the present invention.
Figure 7:
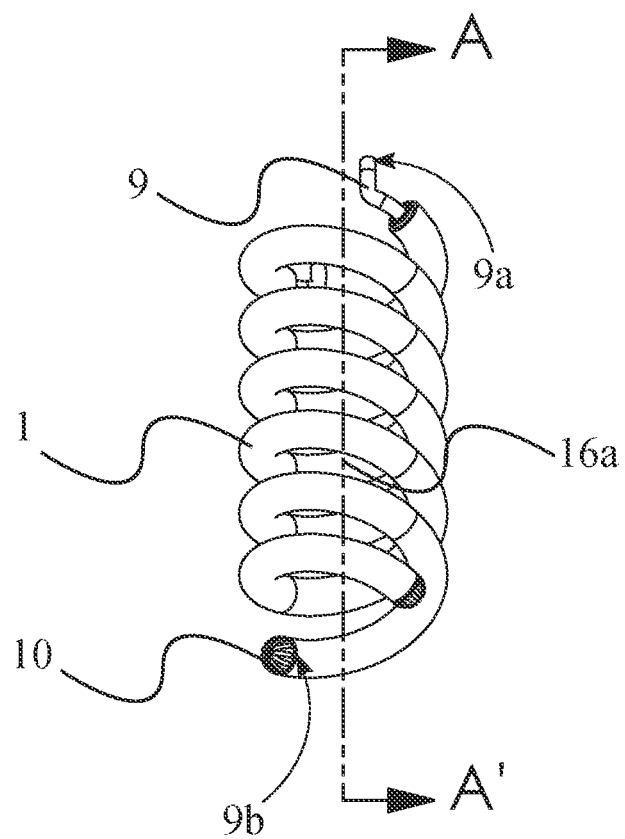
FIG. 7 is a bottom perspective view of a hollow helical rod, wherein a flexible shaft is threaded through the helical rod.

As seen in FIG. 6, the driving unit 2 comprises a housing 12, and a gear assembly 13. As previously mentioned, the driving unit 2 performs the function of generating and transmitting rotational motion to the entire device, as well as the flexible shaft(s) 9. To accomplish this, the gear assembly 13 is mounted within the housing 12, and the rigid shaft 4 is mechanically connected to the gear assembly 13. Further, the flexible shaft 9 is mechanically connected to the gear assembly 13. The rigid shaft 4 may be connected to any external energy source such as a power tool, a motor etc. Thus, the driving unit 2 transmits rotational motion to the flexible shaft 9, thereby transmitting rotational motion and torque along its length to the cutting tool 10.

In this embodiment, the triangular center shaft or rigid shaft 4 may be connected and run by a single motor, and for splitting rotation motion from the rigid shaft 4 to the two flexible shafts, two gears are used, into which the flexible shaft(s) 9 is/are inserted. The orientation of these gear may be horizontal or vertical (as shown in FIG. 6), and the gear types may be helical, bevel, spur, crossed or a combination of the aforementioned.

As seen in FIG. 3 through FIG. 6, the rigid shaft 4 protrudes outside the housing 12 opposite to the helical rod 1. This is so that the rigid shaft 4 may be easily inserted to an external power source. Furthermore, as seen in FIG. 3 through FIG. 6, a lateral side wall 12a of the housing 12 comprises a ridged surface. In other words, the housing 12 of the driving unit 2 may consist of internal/external ridge/teeth features which are used to advance the entire device forwards or backwards into the workpiece in a spiral motion, by rotating the housing manually or automatically (by means of a motor or harmonic/cycloidal drive). The harmonic or cycloidal drives may be utilized to couple the rotation of the housing 12, flexible shafts 9, and rigid shaft 4.

Figure 3:
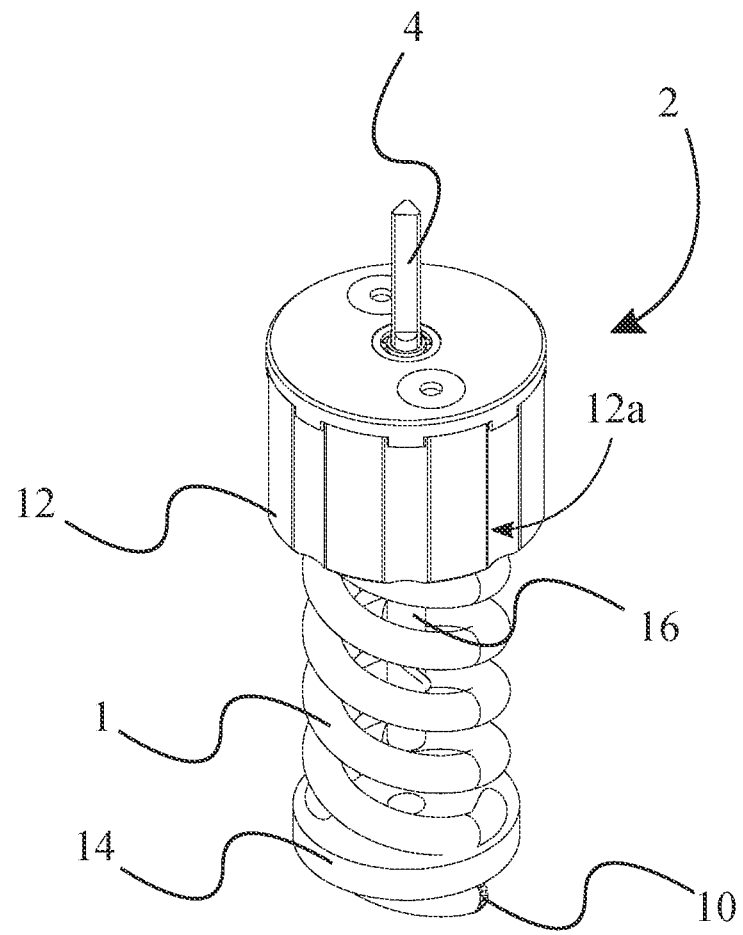
FIG. 3 is a top perspective view of a second embodiment of the present invention, wherein a plurality of cutting tools is positioned adjacent to a lower end of a pair of helical rods.
Figure 4:
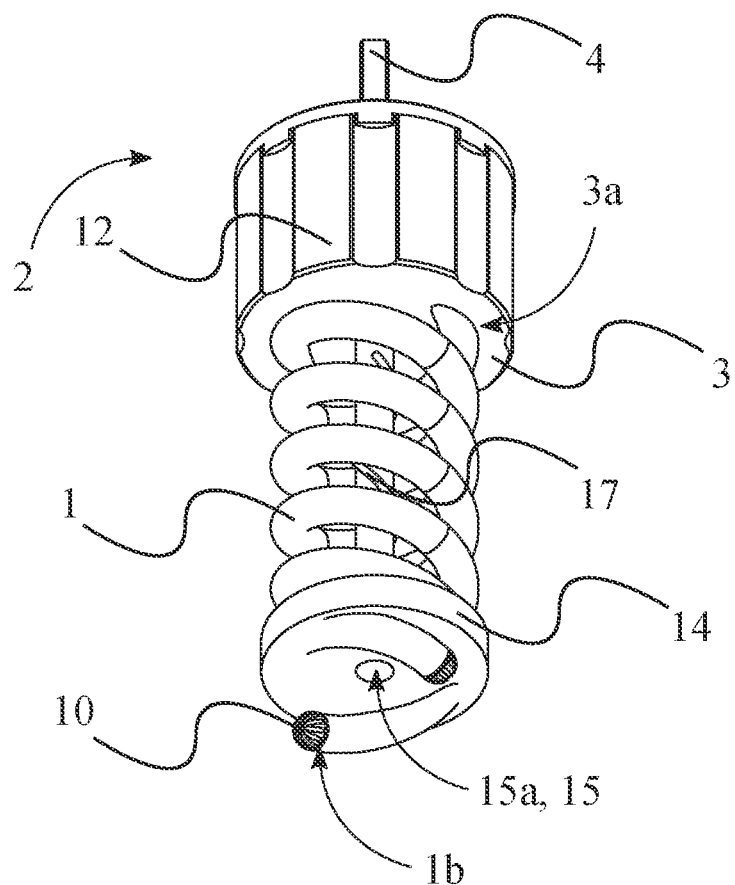
FIG. 4 is a bottom perspective view of the present invention in FIG. 3.
Figure 5:
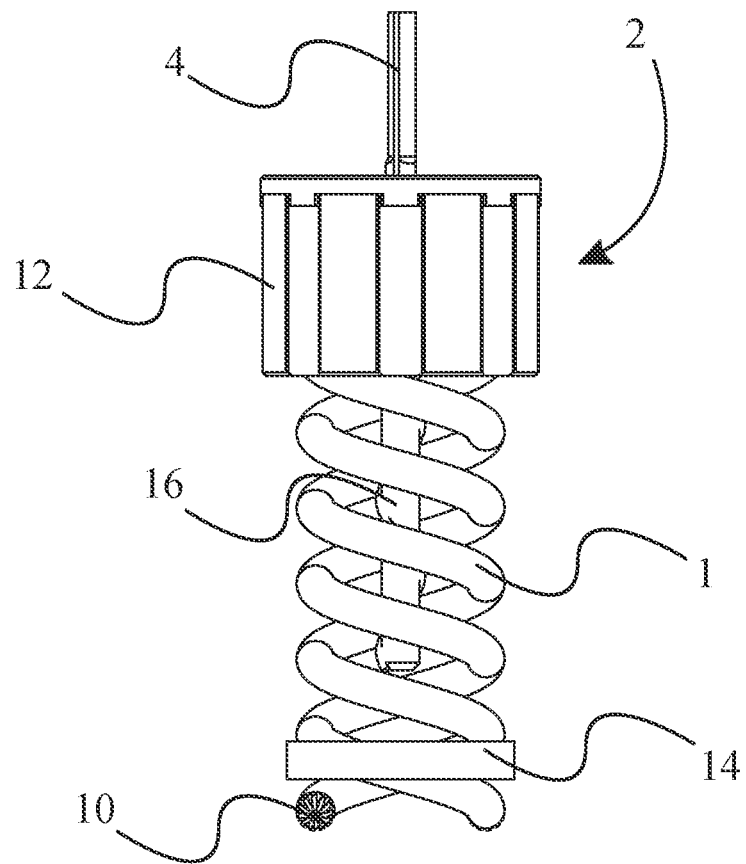
FIG. 5 is a front perspective view of the present invention.

According to this embodiment, the present invention further comprises a stabilizing disc 14, and a plurality of holes 15. Further, the plurality of holes 15 comprises a central hole 15a and a plurality of proximal holes 15b. Preferably, the stabilizing disc 14 is used to provide support along the perimeter of the at least one helical rod 1, increasing its rigidity/stiffness against radial and axial reaction forces during insertion, and is stationary to maintain alignment of the principal axis of the at least one helical rod 1 during tunnelling. As seen in FIG. 6, the plurality of holes 15 traverses through the stabilizing disc 14, and the at least one helical rod 1 is threaded through the stabilizing disc 14. Thus, the at least one helical rod 1 advances through the stabilizing disc 14 as the driving unit 2 rotates the at least one helical rod 1, thereby maintaining axial and radial stability. As seen in FIG. 3 and FIG. 4, the at least one helical rod 1 is threaded through the proximal holes 15b.

In order to maintain alignment of the principal axis of the at least one helical rod 1 during tunnelling, the present invention comprises a cylindrical pin 16. Preferably, the cylindrical pin 16 is positioned along a central principal axis 16a of the at least one helical rod 1, and the cylindrical pin 16 is centrally mounted onto the first surface 3a of the base plate 3. Further, the cylindrical pin 16 is threaded through the central aperture 15a of the stabilizing disc 14. In other words, the cylindrical pin 16 may also be threaded into the stabilizing disc 14, as the same pitch as the helical rod 1, to maintain a consistent advancement of the tunnelling device into the workpiece. Furthermore, the present invention comprises a spring 17, wherein the cylindrical pin 16 is threaded through the spring 17. The spring 17 may also be utilized with or without the cylindrical pin 16, to provide axial dynamic stability, during tunnelling, as well as a returning force for removal of driver after tunnelling. The stabilizing entities may be used independently, or in any combination with each other.

Although the invention has been explained in relation to its preferred embodiment, it is to be understood that many other possible modifications and variations can be made without departing from the spirit and scope of the invention as hereinafter claimed.

What is claimed is:

1. A helical tunneling device, the device comprising:
at least one helical rod;
a driving unit;
the driving unit comprising a base plate and a rigid shaft;
the at least one helical rod comprising a first end and a second end, wherein the first end is positioned opposite to the second end across the at least one helical rod;
a first surface of the base plate being mounted onto the first end of the at least one helical rod;
the rigid shaft being mounted onto a second surface of the base plate, wherein the second surface of the base plate is positioned opposite to the first surface of the base plate across the base plate;
the driving unit being operably coupled to the at least one helical rod, wherein rotating the rigid shaft enables normal advancement and normal retraction of the at least one helical rod along a tunneling surface to create a helical tunnel;
a cavity;
a flexible shaft;
a cutting tool;
the cavity being positioned within the at least one helical rod;
the cavity traversing centrally from the first end through the second end of the at least one helical rod;
the flexible shaft being threaded through the at least one helical rod along the cavity;
a first terminal end of the flexible shaft being mounted onto the driving unit;
the cutting tool being mounted onto a second terminal end of the flexible shaft wherein the first terminal end is positioned opposite to the second terminal end across the flexible shaft;
the cutting tool being positioned outside the at least one helical rod, adjacent to the second end of the at least one helical rod;
a plurality of bearings;
the plurality of bearings being mounted within the cavity;
the flexible shaft being threaded through the plurality of bearings; and
the plurality of bearings being distributed along the at least one helical rod.

2. The helical tunneling device of claim 1, comprising:
the at least one helical rod comprising a plurality of apertures;
the base plate comprising a plurality of protrusions;
the plurality of apertures traversing into the at least one helical rod adjacent the first end of the at least one helical rod;
the plurality of protrusions being mounted on the first surface of the base plate; and
the plurality of protrusions being detachably engaged with the plurality of apertures.

3. The helical tunneling device of claim 1, wherein the cutting tool is a drill bit.

4. The helical tunneling device of claim 1, wherein the flexible shaft conforms to the curvature of the at least one helical rod.

5. The helical tunneling device of claim 1, the driving unit comprising:
a housing;
a gear assembly;
the gear assembly being mounted within the housing;
the rigid shaft being mechanically connected to the gear assembly;

the rigid shaft protruding outside the housing opposite to the at least one helical rod; and the flexible shaft being mechanically connected to the gear assembly.

6. The helical tunneling device of claim 5, wherein a lateral sidewall of the housing comprises a ridged surface.

7. The helical tunneling device of claim 1, comprising:
a stabilizing disc;
a plurality of holes;
the plurality of holes comprising a central hole and a plurality of proximal holes;
the plurality of holes traversing through the stabilizing disc;
the at least one helical rod being threaded through the stabilizing disc;
the at least one helical rod advancing through the stabilizing disc as the driving unit rotates the at least one helical rod.

8. The helical tunneling device of claim 7, comprising:
a cylindrical pin;
a spring;
the cylindrical pin being centrally mounted onto the first surface of the base plate;
the cylindrical pin being positioned along a central principal axis of the at least one helical rod; and
the cylindrical pin being threaded through the spring.

9. The helical tunneling device of claim 8, wherein the cylindrical pin being threaded through the central hole of the plurality of holes.

10. The helical tunneling device of claim 7, wherein the at least one helical rod being threaded through the plurality of proximal holes.

11. A helical tunneling device, the device comprising:
at least one helical rod;
a driving unit;
a cavity;
a flexible shaft;
a cutting tool;
the driving unit comprising a base plate and a rigid shaft;
the cavity being positioned within the at least one helical rod;
the at least one helical rod comprising a first end and a second end, wherein the first end is positioned opposite to the second end across the at least one helical rod;
the cavity traversing centrally from the first end through the second end of the at least one helical rod;
the flexible shaft being threaded through the at least one helical rod along the cavity;
a first terminal end of the flexible shaft being mounted onto the driving unit;
the cutting tool being mounted onto a second terminal end of the flexible shaft wherein the first terminal end is positioned opposite to the second terminal end across the flexible shaft;
the cutting tool being positioned outside the at least one helical rod, adjacent to the second end of the at least one helical rod;
a first surface of the base plate being mounted onto the first end of the at least one helical rod;
the rigid shaft being mounted onto a second surface of the base plate, wherein the second surface of the base plate is positioned opposite to the first surface of the base plate across the base plate;
the driving unit being operably coupled to the at least one helical rod, wherein rotating the rigid shaft enables normal advancement and normal retraction of the at least one helical rod along a tunneling surface to create a helical tunnel;
a plurality of bearings;
the plurality of bearings being mounted within the cavity;
the flexible shaft being threaded through the plurality of bearings;
the plurality of bearings being distributed along the at least one helical rod;
a stabilizing disc;
a plurality of holes;
a cylindrical pin;
a spring;
the cylindrical pin being centrally mounted onto the first surface of the base plate;
the cylindrical pin being positioned along a principal axis of the at least one helical rod;
the cylindrical pin being threaded through the spring;
the plurality of holes traversing through the stabilizing disc;
the at least one helical rod being threaded through the stabilizing disc; and
the at least one helical rod advancing through the stabilizing disc as the driving unit rotates the at least one helical rod.

12. The helical tunneling device of claim 11, the driving unit comprising:
a housing;
a gear assembly;
the gear assembly being mounted within the housing;
the rigid shaft being mechanically connected to the gear assembly;
the rigid shaft protruding outside the housing opposite to the at least one helical rod;
the flexible shaft being mechanically connected to the gear assembly.

13. The helical tunneling device of claim 12, wherein a lateral sidewall of the housing comprises a ridged surface.

14. The helical tunneling device of claim 11, wherein the cutting tool is a drill bit.

15. The helical tunneling device of claim 11, wherein the flexible shaft conforms to the curvature of the at least one helical rod.

16. A helical tunneling and fixation device, the device comprising:
at least one helical rod;
a driving unit;
the at least one helical rod comprising a plurality of apertures;
the driving unit comprising a base plate and a rigid shaft;
the base plate comprising a plurality of protrusions;
the at least one helical rod comprising a first end and a second end, wherein the first end is positioned opposite to the second end across the at least one helical rod;
a first surface of the base plate being mounted onto the first end of the at least one helical rod;
the rigid shaft being mounted onto a second surface of the base plate, wherein the second surface of the base plate is positioned opposite to the first surface of the base plate across the base plate;
the plurality of apertures traversing into at least one helical rod adjacent the first end of the at least one helical rod;
the plurality of protrusions being mounted on the first surface of the base plate;
the plurality of protrusions being detachably engaged with the plurality of apertures;

the driving unit being operably coupled to the at least one helical rod, wherein rotating the rigid shaft enables normal advancement and normal retraction of the at least one helical rod along a tunneling surface to create a helical tunnel;

a cavity;

a flexible shaft;

a cutting tool;

the cavity being positioned within the at least one helical rod;

the cavity traversing centrally from the first end through the second end of the at least one helical rod;

the flexible shaft being threaded through the at least one helical rod along the cavity;

a first terminal end of the flexible shaft being mounted onto the driving unit;

the cutting tool being mounted onto a second terminal end of the flexible shaft wherein the first terminal end is positioned opposite to the second terminal end across the flexible shaft;

the cutting tool being positioned outside the at least one helical rod, adjacent to the second end of the at least one helical rod;

a plurality of bearings;

the plurality of bearings being mounted within the cavity;

the flexible shaft being threaded through the plurality of bearings;

the plurality of bearings being distributed along the at least one helical rod;

a stabilizing disc;

a plurality of holes;

the plurality of holes comprising a central hole and a plurality of proximal holes;

the plurality of holes traversing through the stabilizing disc;

the at least one helical rod being threaded through the stabilizing disc;

the at least one helical rod advancing through the stabilizing disc as the driving unit rotates the at least one helical rod;

a cylindrical pin;

a spring;

the cylindrical pin being centrally mounted onto the first surface of the base plate;

the cylindrical pin being positioned along a central principal axis of the at least one helical rod;

the cylindrical pin being threaded through the spring; and the cylindrical pin being threaded through the central hole of the plurality of holes.

\* \* \* \* \*